(12) United States Patent
Cihan et al.

(10) Patent No.: US 11,419,546 B2
(45) Date of Patent: Aug. 23, 2022

(54) WEARABLE SELF-MIXING INTERFEROMETRY DEVICE USED TO SENSE PHYSIOLOGICAL CONDITIONS

(71) Applicant: Apple Inc., Cupertino, CA (US)

(72) Inventors: Ahmet Fatih Cihan, Stanford, CA (US); Adrian Z. Harb, Cupertino, CA (US); Mehmet Mutlu, Stanford, CA (US); Mengshu Huang, Cupertino, CA (US); Stephen E. Dey, Cupertino, CA (US); Yuhao Pan, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 399 days.

(21) Appl. No.: 16/581,695

(22) Filed: Sep. 24, 2019

(65) Prior Publication Data

US 2021/0085245 A1   Mar. 25, 2021

(51) Int. Cl.
| | | |
|---|---|---|
| *A61B 5/04* | (2006.01) | |
| *A61B 5/00* | (2006.01) | |
| *G06F 1/16* | (2006.01) | |
| *A61B 5/24* | (2021.01) | |
| *H01S 5/183* | (2006.01) | |

(52) U.S. Cl.
CPC .............. *A61B 5/4884* (2013.01); *A61B 5/24* (2021.01); *A61B 5/441* (2013.01); *G06F 1/163* (2013.01); *H01S 5/183* (2013.01)

(58) Field of Classification Search
CPC ... A61B 5/02427; A61B 5/02438; A61B 5/24; A61B 5/6802; A61B 5/6826; G06F 1/163; H01S 5/183
See application file for complete search history.

(56) References Cited

U.S. PATENT DOCUMENTS

| | | |
|---|---|---|
| 4,746,770 A | 5/1988 | McAvinney |
| 5,914,704 A | 6/1999 | Yamada et al. |
| (Continued) | | |

FOREIGN PATENT DOCUMENTS

| | | |
|---|---|---|
| DE | 102016211983 | 1/2018 |
| WO | WO 99/030311 | 6/1999 |
| (Continued) | | |

OTHER PUBLICATIONS

Liess et al., "A miniaturized multidirectional optical motion sensor and input device based on laser self-mixing," Measurement Science and Technology, Institute of Physics Publishing, Bristol, GB, 2002, vol. 13, No. 12, pp. 2001-2006.

*Primary Examiner* — Jon Eric C Morales
(74) *Attorney, Agent, or Firm* — Brownstein Hyatt Farber Schreck, LLP

(57) ABSTRACT

A wearable electronic device including a housing that is worn by a user and a SMI sensor contained within the housing. The SMI sensor may include an emitter that outputs coherent light toward the skin of a user when the housing is worn by the user. The SMI sensor may also include a detector that detects a portion of the coherent light reflected towards the sensor and generates electrical signals that indicate displacements of the skin based on the portion of coherent light received at the detector. The housing may include a transmitter that is operatively coupled with the SMI sensor and is configured to transmit physiological data to a receiving device based on electrical signals output from the SMI sensor.

19 Claims, 11 Drawing Sheets

(56) References Cited

U.S. PATENT DOCUMENTS

| | | |
|---|---|---|
| 6,178,001 B1 | 1/2001 | Kim |
| 7,126,586 B2 | 10/2006 | Jianping et al. |
| 7,535,578 B2 | 5/2009 | Pril |
| 7,880,732 B2 | 2/2011 | Goertz |
| 8,368,652 B2 | 2/2013 | Lin |
| 8,416,424 B2 | 4/2013 | Werner |
| 8,945,017 B2 | 2/2015 | Venkatraman et al. |
| 9,880,632 B2 | 1/2018 | Ataee et al. |
| 9,912,923 B2 | 3/2018 | Kilcher et al. |
| 10,117,012 B2 | 10/2018 | Saulsbury |
| 10,126,779 B2 | 11/2018 | von Badinski et al. |
| 10,317,940 B2 | 6/2019 | Eim |
| 10,379,028 B2 | 8/2019 | Spruit et al. |
| 10,401,901 B2 | 9/2019 | Park |
| 10,768,693 B2 | 9/2020 | Powderly et al. |
| 10,838,499 B2 | 11/2020 | Wang et al. |
| 2002/0104957 A1 | 8/2002 | Liess |
| 2007/0077900 A1 | 4/2007 | Grunhlke |
| 2008/0188726 A1 | 8/2008 | Presura |
| 2008/0200781 A1 | 8/2008 | Van Herpen |
| 2010/0081900 A1 | 4/2010 | Price |
| 2010/0134803 A1 | 6/2010 | Baier |
| 2010/0328680 A1 | 12/2010 | Moench et al. |
| 2011/0105874 A1 | 5/2011 | Feddes |
| 2012/0120375 A1 | 5/2012 | Kilcher |
| 2012/0160031 A1 | 6/2012 | Van Steenberge |
| 2012/0200858 A1 | 8/2012 | Pruijmboom |
| 2013/0053696 A1 | 2/2013 | Hasgawa-Johnson |
| 2014/0085635 A1 | 3/2014 | Van Der Lee |
| 2015/0286293 A1 | 10/2015 | Gruhlke et al. |
| 2015/0366518 A1* | 12/2015 | Sampson ............ A61B 5/0261 |
| | | 600/301 |
| 2016/0062473 A1 | 3/2016 | Bouchat et al. |
| 2016/0120468 A1 | 5/2016 | Mathew |
| 2016/0320173 A1 | 11/2016 | Royo Royo |
| 2017/0085688 A1 | 3/2017 | Zhou |
| 2017/0090581 A1 | 3/2017 | Pothier |
| 2017/0248422 A1 | 8/2017 | Najafi |
| 2018/0115439 A1 | 4/2018 | Bhatti |
| 2018/0157342 A1 | 6/2018 | Romano |
| 2018/0310891 A1 | 11/2018 | Fine |
| 2019/0034072 A1 | 1/2019 | Chiu |
| 2019/0056498 A1 | 2/2019 | Sonn |
| 2019/0285753 A1 | 9/2019 | Spruit |
| 2019/0324536 A1 | 10/2019 | Forest et al. |
| 2019/0332140 A1 | 10/2019 | Wang |
| 2019/0357771 A1 | 11/2019 | Yu |
| 2020/0200522 A1 | 6/2020 | Huang |
| 2020/0264311 A1 | 8/2020 | Le Dortz et al. |
| 2021/0011559 A1 | 1/2021 | Mutlu et al. |
| 2021/0072833 A1 | 3/2021 | Mutlu et al. |

FOREIGN PATENT DOCUMENTS

| | | |
|---|---|---|
| WO | WO 03/102625 | 12/2003 |
| WO | WO 08/055640 | 5/2008 |
| WO | WO 09/004559 | 1/2009 |

* cited by examiner

WEARABLE SELF-MIXING INTERFEROMETRY DEVICE USED TO SENSE PHYSIOLOGICAL CONDITIONS

FIELD

Embodiments described herein relate generally to devices that include self-mixing interferometry sensors and, more particularly, to wearable devices that use one or more self-mixing interferometry sensors to sense a movement of the skin of a user and/or determine one or more physiological conditions, such as a heart rate, from the movement of the skin.

BACKGROUND

Electronic devices, such as smartphones, watches, and other wearable devices, may include sensor systems to detect and/or monitor one or more physiological conditions of a user. Wearable electronic device may measure and/or monitor heart rates, blood oxygen saturation, blood pressure, sleep cycles, body temperatures, and so on. These electronic devices may include one or more sensor systems that derive a physiological condition of the user (e.g., blood oxygen saturation, heart rate, and so on) by applying a stimulus such as light and detecting a response from the stimuluses interaction with the body. Sensor systems may use a light emitting diodes (LEDs) to transmits light such as infrared light into the a blood vessel and detect the response of the light after interacting with the blood. In such cases, one or more conditions of the blood (e.g., flow rate, oxygen content, and so on) may affect the transmitted light, which may be used to derive a physiological parameter such as a blood oxygen saturation. In many cases, the accuracy and/or quality of measurements from these sensor systems depends on light being transmitted into the skin to interact with one or more blood vessels. Thus, these sensors may be sensitive to positioning on the user and or require robust circuitry to detect and/or processes the signals received from a user's body.

SUMMARY

Embodiments of the systems, devices, methods, and apparatus described in the present disclosure are directed to the configuration and operation of a device that includes an electronic device having one or more self-mixing interferometry sensors. The self-mixing interferometry sensor(s) may be used to measure one or more physiological conditions of a user. The electronic device may include a housing configured to be worn by a user and a sensor contained within the housing. The sensor may include an emitter positioned within the housing and configured to output coherent light toward a skin of the user when the housing is worn by the user. The sensor may also include a detector configured to detect a portion of coherent light reflected towards the sensor and generate electrical signals that indicate displacements of the skin based on the portion of coherent light. The electronic device may further include a transmitter operatively coupled with the sensor and configured to transmit physiological data based on the electrical signals.

Embodiments may further be directed to an electronic device including a sensor where the sensor includes an emitter configured to output coherent light toward a skin of a user when the electronic device is worn by the user, and a detector configured to detect a portion of the coherent light reflected from the user and generate electrical signals based on the portion of the coherent light. The electronic device may also include a housing containing the sensor and configured to position the emitter at a first distance from the skin of a user. The housing may include a user interface configured to contact the skin of the user. The electronic device may further include a transmitter positioned within the housing and operatively coupled with the sensor. The transmitter may be configured to transmit physiological data based on the electrical signals.

Additional embodiments may be directed to a method for tracking movement of the skin of a user. The method may include transmitting coherent light from a self-mixing interferometer (SMI) and towards a skin surface of a user; detecting a portion of the coherent light reflected towards the SMI; generating, at the SMI, an electrical signal based on the detected portion of the coherent light; determining displacements of the skin based on the detected portion of the coherent light; and outputting a heart rate for the user based on the displacements of the skin.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

Figure 1:
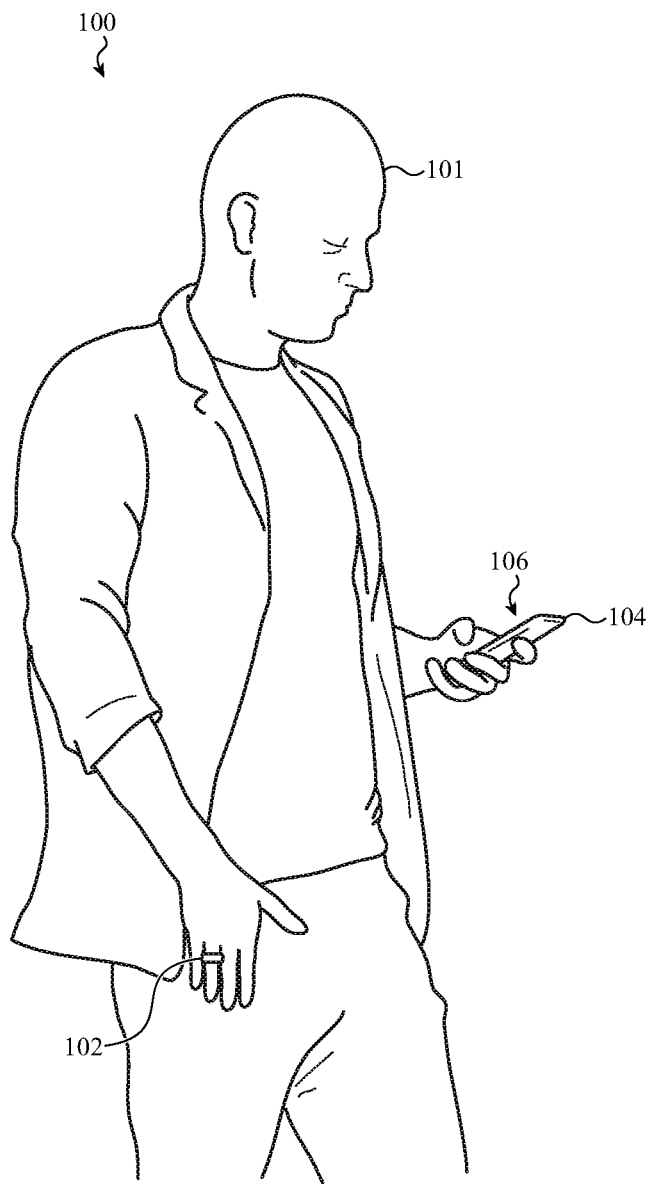
FIG. 1 shows an example of a physiological monitoring system that includes a wearable device and an electronic device.

The detailed description set forth below is intended as a description of various configurations of the subject technology and is not intended to represent the only configurations in which the subject technology may be practiced. The appended drawings are incorporated herein and constitute part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in a block diagram form in order to avoid obscuring the concepts of the subject technology.

Embodiments described herein are generally directed to electronic devices incorporating self-mixing interferometer (SMI) sensors that are configured to detect one or more physiological conditions of a user. As health tracking applications, remote patient monitoring, and telemedicine are becoming more widely available, remote monitoring is becoming increasingly important tools for detecting and monitoring physiological conditions of a user. Many conventional physiological monitors such as device for measuring heart rates, oxygen saturation, and so on rely on an interaction between an emitted stimulus and a blood volume of a user. In such cases, the detection mechanism may rely on light passing through a skin of a user, into the body, and then to back out to a detector located outside the body. Thus, many conventional devices require complex sensing hardware and analysis methods to derive a physiological condition of the user. Further, traditional detection procedures (e.g., measuring absorbance of light by the body) may be limited to specific locations on the body such as a fingertip. These requirements of typical devices can limit normal movement of the user while using the device and/or require a user to remain relatively motionless during the measurement process.

Due to the ability to measure micron or submicron displacement changes and the ability to make measurements in a variety of situations, an SMI sensor (or multiple SMI sensors) can be used to measure physiological conditions of a user. Unlike conventional physiological monitors, an SMI device may output a signal that interacts with the skin of user, and thus, may be placed in a variety of locations on a user's body. Further, the smaller size of SMI based sensors as compared to other conventional device allows them to be placed in smaller wearable devices that interfere less with the normal movements/functioning of a user. Accordingly, wearable SMI devices may be worn over longer durations with minimal effect on a user's normal movements and may monitor one or more physiological conditions over these extended durations.

A wearable electronic device may include one or more SMI sensors located within a housing and configured to detect a physiological condition of a wearer. Sample wearable devices include rings, watches, glasses, headbands, earrings, and the like. In other embodiments, the electronic device may not be wearable but may instead be incorporated with a device configured to contact a user's skin, such as smartphones, tablets, earbuds, laptops, exercise equipment, steering wheels and the like. The housing may include one or more structures that position the SMI sensor relative to the skin and/or hold the SMI sensor in a stable orientation relative to the skin. The SMI sensor may detect displacements of the skin relative to the sensor, such as expanding and contracting of skin due to a user's heartbeat. In some cases, the housing may set and/or maintain a gap between an emitter portion of the SMI sensor and a skin surface of a user to ensure that movement of the skin is not inhibited by the SMI sensor or other portions of the housing. The wearable electronic device may transmit physiological data collected from the SMI sensor to one or more other electronic devices such as a smartphone, smart watch, tablet, computing device, or the like. The data collected by the wearable device may be used to determine one or more physiological conditions for a user such as a heart rate.

These and other techniques are described with reference to FIGS. 1-9. However, those skilled in the art will appreciate that the detailed description given herein with respect to these figures is for exemplary purposes and should not be construed as limiting.

FIG. 1 shows an example of a physiological monitoring system 100 that includes a wearable device 102 and an electronic device 104 that may electronically communicate with the wearable device 102. The wearable device 102 may include a housing containing an SMI sensor that is oriented toward a skin surface of a user 101 when the device 102 is worn by the user 101. The SMI sensor may transmit light toward the skin of the user 101 and detect a portion of the light reflected from the user 101 (whether from a surface of the user's skin, blood vessels within the skin, or other tissues within or beneath the skin), which may be used to detect and/or monitor one or more physiological conditions of the user 101. The wearable device 102 may send signals and/or physiological data to the electronic device 104, which may display information, process information, transmit information or perform various other functions using the physiological data. For example, the electronic device 104 may output a visual indication of detected heartbeats on the electronic device 104 screen, output a haptic feedback such as a short vibration to stimulate a user 101 based on detected heartbeats, launching an application, sending out an emergency signal, and so on.

In one non-limiting example the wearable device 102 may include one or more SMI sensors and a housing; the SMI sensor may emit coherent light through the housing and onto the skin of the user. The SMI sensor may generate electrical outputs that are based on detecting a portion of coherent light reflected back from the user. In some cases, the wearable device 102 may also include one or more integrated chips such as an application-specific integrated circuit (ASIC) or processing unit that is electrically coupled with the SMI sensor and processes electrical signals received from the SMI sensor. The integrated chip may include or be coupled with a transmitter and/or transceiver integrated into the wearable device 102. The integrated chip and transmitter and/or transceiver may send and receive data to the electronic device 104 based on outputs received from the SMI sensor. In some cases, a processor or integrated chip is housed in the wearable device 102 and computes a physiological condition such as a heart rate for the user 101. A transmitter/transceiver may transmit the heart rate value to the electronic device 104. Additionally or alternatively, the wearable device 102 (and particularly, the integrated chip and/or transceiver) may transmit raw data (e.g., electrical signals and/or digital versions of the electrical signals generated by the SMI sensor) to the electronic device 104 and the electronic device 104 may compute a physiological condition (e.g., heart rate). The SMI sensor is discussed in more detail below with respect to FIG. 2.

The electronic device 104 may be a smartphone, smart watch, tablet computing device, personal digital assistant, laptop computing device, media player, remote control, or other personal computing device that receives physiological data from the wearable device 102 and (optionally) processes the physiological data to provide output to the user (e.g., display a heart rate, provide a haptic feedback based on a detected physiological parameter, or the like). The electronic device 104 may also include a gateway or routing device that receives the physiological data from the wearable device 102 and sends to the data to a remote system such as a remote patient monitoring system or telemedicine system.

The wearable device 102 and/or electronic device 104 may include an output on which graphical outputs are displayed. Graphical outputs may include graphical user interfaces, user interface elements (e.g., buttons, sliders, etc.), texts, lists, photographs, videos, or the like. The output region may include a display such as a liquid-crystal display (LCD), organic light emitting diode display (OLED), or any other suitable components or display technology.

The electronic device 104 may establish a communications connection, such as a wireless connection, with the wearable device 102 to receive data or other communications from the wearable device 102 and/or control one or more operating parameters of the wearable device 102. For example, the electronic device 104 may activate the SMI sensor to begin a physiological monitoring process, such as determining a heart rate and/or blood pressure for the user. In some examples, the electronic device 104 may change a sampling frequency, initiate a haptic feedback mechanism in the wearable device 102, control display elements (e.g., OLED display integrated into the wearable device, one or more status indicator lights, or the like), control speaker components integrated into the wearable device 102, monitor a battery state of the wearable device 102, and so on.

The wearable device 102 and/or electronic device 104 may also include input structures such as switches, buttons, touch screen inputs, voice inputs, and so on. For example, the wearable device 102 and/or electronic device 104 may include or be associated with touch sensors and/or force sensors (e.g., integrated into one or more displays of these devices). The input structures of the devices 102, 104 may detect force and/or touch inputs, whether static or motions, speed, direction, force, displacement, or other parameters of gestures applied to the input regions, including taps, swipes, multi-finger inputs, single- or multi-finger touch gestures, presses, and the like. Such user inputs may be used to control or modify the operation of the device. The input regions may control various aspects of the wearable device 102 and/or the electronic device 104. For example, the input structures may be used to select icons, items, or other objects presented on a display, to activate or deactivate functions (e.g., begin a detecting process, silence an alarm, and so on), or the like. In some cases, an input provided to the electronic device 104 may initiate a signal to the wearable device 104, such as to initiate a physiological detection process at the wearable device 102.

Figure 2:
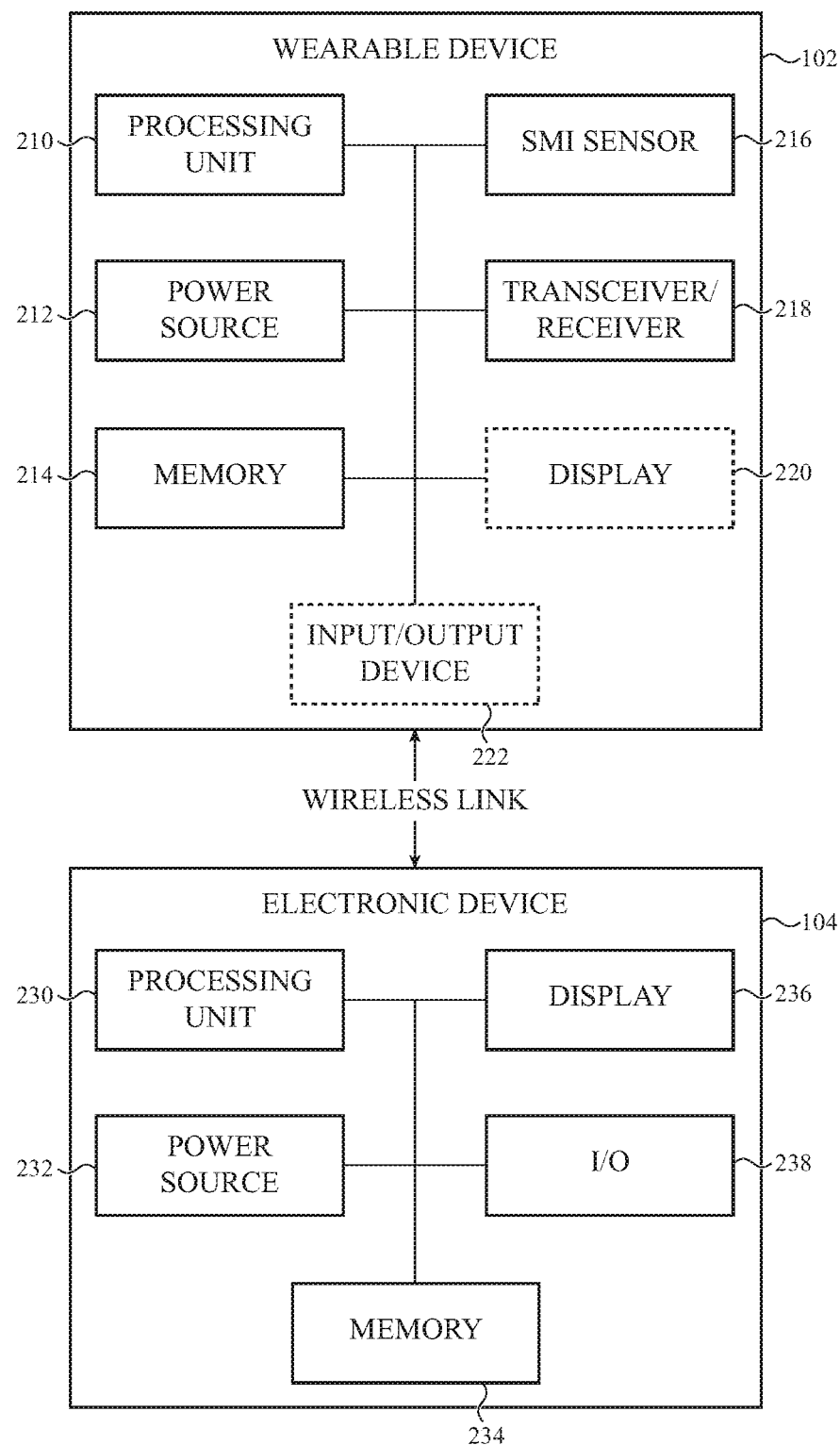
FIG. 2 is a block diagram illustrating an example of a physiological monitoring system that includes a wearable device and an electronic device.

FIG. 2 is a block diagram illustrating an example of a physiological monitoring system that includes a wearable device 102 and an electronic device 104. As shown in FIG. 2 the wearable device 102 includes a processing unit 210 operatively coupled with a power source 212 and memory 214. The processing unit 210 may take the form of one or more computer processing units or microcontrollers that are configured to perform operations in response to computer-readable instructions, or other processing components such as an ASIC. The processing unit 210 may be operatively coupled with the memory 214 via one or more electrical connections such as an electronic bus or bridge. In some cases, the processing unit 210 and memory may be integrated on a single chip.

The wearable device 102 may also include a SMI sensor 216 and a transmitter and/or receiver 218 (hereafter referred to as a "transceiver") for communicating with the electronic device 104. The SMI sensor 216 and transceiver 218 may be operatively coupled with the processing unit 210 via an electronic bus, bridge, flex connection, and so on. One or more functions of the SMI sensor 216 may be controlled by the processing unit 210 such as activating a detection process. The processing unit 210 may also receive electrical outputs from the SMI sensor 216 and process these inputs to be transferred to the electronic device 104 (e.g., via transceiver 218). The transceiver 218 may include one or more radios, antennas, or other components for wirelessly transmitting and/or receiving communications with the electronic device 104.

The SMI sensor 216 may include an emitter and a detector and output electrical signals based on displacements, velocities, or movement of a skin surface of a user relative to the SMI sensor. The emitter may be a vertical cavity surface emitting laser (VCSEL) that outputs coherent light, which may be visible light, infrared light, or ultraviolet light. Coherent light may include complete or substantially complete coherent light, partially coherent light or semi-coherent light. The detector may include a separate photodiode or be part of the VCSEL structure itself. For example, the detector may include a VCSEL with an integrated intra-cavity or extra-cavity photodetector that has an absorbing photodetecting layer positioned within the VCSEL structure.

The SMI sensor 216 may emit coherent light from a stimulated emission source, and detect a portion of the emitted coherent light that is reflected from a target (e.g., skin of a user) and back toward the SMI sensor 216. The portion of reflected light may enter the emitter cavity and interfere with light generated inside the emitter to cause changes in the optical and electrical properties of the emitter (e.g., amplitude and frequency of the coherent light may bias current or voltage of the emitter). The changes in these optical properties can be used to determine a distance, displacement or velocity of a target. The SMI sensor 216 may output an electrical signal that indicates one or more of a distance, displacement or velocity of the target based on the interference created by the portion of reflected coherent light.

In some cases, the wearable device 102 may include a display 220 and one or more input/output devices 222. The display 220 and input/output device(s) 222 may be operatively coupled with the processing unit 210. The display 220 may provide visual outputs based on one or more physiological parameters detected by the SMI device 216 and/or in response to instructions from the processing unit 210. For example, the display 220 may show a heart rate to a user of the device. As another example, the display 220 may include one or more lights that blink or flash based on a heartbeat of the user detected by the wearable device 102. In some cases, the wearable device 102 may include a haptic feedback mechanism and apply a stimulus, such as a vibration, to a user wearing the wearable device 102.

In some embodiments, the wearable device 102 includes one or more input devices 222 that are configured to receive a user input. The one or more input devices 222 may include, for example, a push button, a touch activated interface, a force activated interface, and so on. In some embodiments, the input device 222 may provide a dedicated primary function, including, for example, powering the device on or off, beginning/ending a physiological detection or monitoring procedure, initiating a display function such as displaying physiological data (e.g., a heart rate), and/or initiating a transfer of physiological data to or from the electronic device.

In some embodiments, the wearable device 102 includes one or more output devices 222 configured to produce an output that is perceivable by a user. The one or more output devices 222 may include, for example, a speaker, light sources (e.g., an indicator light), an audio transducer, a haptic actuator, or the like.

As shown in FIG. 2, the electronic device 104 includes a processing unit 230 operatively coupled with a power source 232 and memory 234. The processing unit 230 may include one or more computer processing units, microcontrollers or other processing units (such as an ASIC, microprocessor, system-on-chip, field-programmable gate array, or the like) that are configured to perform operations in response to computer-readable instructions or other inputs. The processing unit 230 may be operatively coupled with the memory 234 via one or more electrical connections such as an electronic bus or bridge. In some cases, the processing unit 230 and memory may be integrated on a single chip.

The electronic device 104 may also include a display 236 and one or more input/output devices 238. The display 236 may define an output region in which graphical outputs are displayed. Graphical outputs may include graphical user interfaces, user interface elements (e.g., buttons, sliders, etc.), text, lists, photographs, videos, or the like. The display 236 may include a liquid-crystal display (LCD), organic light emitting diode display (OLED), or any other suitable components or display technology. The display 236 may include or be associated with touch sensors and/or force sensors that extend along the output region of the display and which may use any suitable sensing elements and/or sensing techniques. Using touch sensors, the device 100 may detect touch inputs applied to a cover, including detecting locations of touch inputs, motions of touch inputs (e.g., the speed, direction, or other parameters of a gesture applied to the cover), or the like. Using force sensors, the electronic device 104 may detect amounts or magnitudes of force associated with touch events applied to the cover. The touch and/or force sensors may detect various types of user inputs to control or modify the operation of the device, including taps, swipes, multi-finger inputs, single- or multi-finger touch gestures, presses, and the like. Touch and/or force sensors usable with wearable electronic devices, such as the electronic device 104, are described below In some embodiments, the electronic device 104 includes one or more input devices 238. An input device 238 is a device that is configured to receive user input. The one or more input devices 238 may include, for example, a touch sensor, a force sensor, a push button, a touch-activated button, a keyboard, a key pad, or the like (including any combination of these or other components). In some embodiments, the input device 238 may provide a dedicated or primary function, including, for example, a power button, volume buttons, home buttons, scroll wheels, and camera buttons. Generally, a touch sensor or a force sensor may also be classified as an input device.

In some embodiments, the device 104 includes one or more output devices 238. An output device 238 is a device that is configured to produce an output that is perceivable by a user. The one or more output devices 238 may include, for example, a speaker, a light source (e.g., an indicator light), an audio transducer, a haptic actuator, or the like.

The wearable device 102 and the electronic device 104 may establish wired and/or wireless communications links to transfer data, control aspects of a detection/monitoring procedure, transmit status updates, send commands, and so on.

Figure 3:
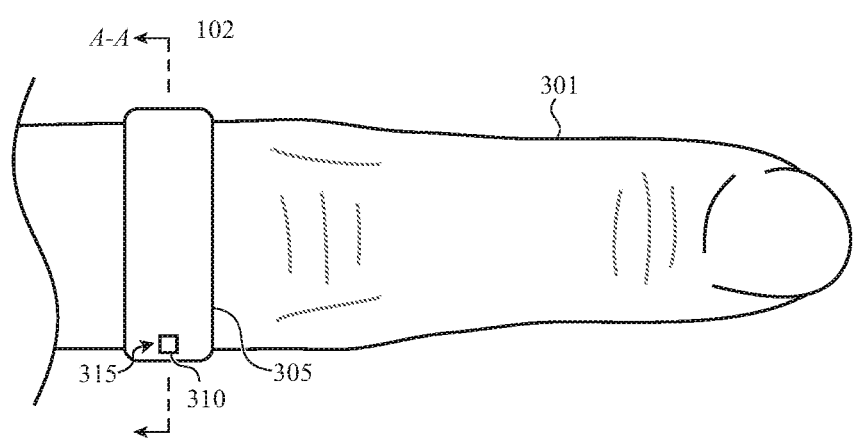
FIG. 3 shows an example of a wearable device that includes an SMI sensor and is positioned on a finger of a user.

FIG. 3 illustrates an example of a wearable device 102 taking the form of a ring that can be worn on a finger 301 of a user. The ring 102 includes a housing 305 and an SMI sensor 310 configured to emit and detect coherent light. The housing 305 is coupled with the SMI sensor 310 such that the SMI sensor 310 emits coherent light towards the skin of a user when the ring 102 is worn on the finger 301. In some cases, the housing may be coupled with multiple SMI sensors 310, and each sensor may emit coherent light toward different regions of skin.

The SMI sensor 310 may be coupled/with the housing 305 such that the region of skin illuminated by emitted coherent light is able to expand and contract relative to the SMI sensor 310. For example, the SMI sensor 310 may be coupled to the housing 305 and offset from an inner diameter of the housing by a gap 315. This gap 315 separates the SMI sensor 310 from the skin. Accordingly, coherent light emitted from the SMI sensor 310 may travel across the gap 315 before intersecting the surface of the skin. The skin may expand and contract within the gap (e.g., in response to a user's heart beat) changing the distance between the SMI sensor 310 and the skin. The SMI sensor 310 may detect these changes in distance from the skin based on emitting coherent light toward the skin and detecting the portion of coherent light reflected back from the skin.

The housing 305 and SMI sensor 310 may be coupled in a variety of ways, and in some examples, include structures or other components that maintain a gap between the SMI sensor 310 (or a portion of the SMI sensor 310 such as the emitter and/or detector) and the surface of the skin. In some cases, the housing 305 may define one or more structures that contain and/or offset the SMI sensor 310 from the finger 301 to maintain the gap 315 between the SMI sensor 310 and the skin. In further examples, the ring 102 may include one or more structures coupled with the housing 305 and positioned between the SMI sensor 310 and the skin to maintain a gap between the SMI sensor 310 and the skin. These, as well as other embodiments, are described in greater detail herein.

The housing 305, or a portion of the housing 305, may be formed from a single material or a combination of different materials. For example the housing 305 may define a circular band formed from a metal such as gold, platinum, silver, steel, aluminum, titanium, alloy, or combination thereof. In some embodiments, the housing 305 or a portion of the housing 305 may be formed from materials, including polymers, vulcanized rubbers, ceramics, or the like. In some examples, a first portion of the housing 305 (e.g., a band portion) may be formed from a first material such as a metal and a second portion of the housing 305 (e.g., a portion containing the SMI sensor 310) may be formed from a second material such as a transparent polymer, glass, crystalline, ceramic or other suitable material.

In some cases, the SMI sensor 310 is contained within the housing 305. For example, the housing 305 may define a cavity or volume that contains the SMI sensor 310. In some cases, this cavity may be substantially the size of the SMI sensor 310. In other cases, the cavity may be larger than the SMI sensor 310, such as an annulus that extends around an inside surface of the housing 305. In such embodiments, the SMI sensor 310 may occupy a portion of the cavity. In further embodiments, a cavity defined by the housing 305 may also contain other components of the ring 102, such as a battery, transceiver, processing unit, display(s), haptic feedback mechanism(s), or the like, or any combination thereof. In other embodiments, the housing 305 may define a channel through which the SMI sensor may emit light toward and/or onto a user's skin. All of the foregoing embodiments facilitate emitting light from, and receiving reflected light at, the SMI sensor 310.

The housing 305 may be formed from an assembly of components that are coupled together to form a ring structure. For example, the housing 305 may include an annular ring portion made from a first material such as a metal. This annular ring portion may define one or more cutouts or cavities that house different components. For example, a display apparatus such as an OLED display, a touch sensitive display, one or more indicator lights or the like may be positioned within the first cavity. In some cases, the housing 305 may contain structures for coupling one or more other components to the ring 102. For example, the housing may contain prongs to couple a decorative element such as a diamond to the ring 102.

In some cases, the SMI sensor 310 may be sealed within the housing 305. The SMI sensor 310 faces inward on the housing 305 such that light is emitted toward a center of the ring 102. In some cases, the housing 305 may take on a toroid shape and the SMI sensor may be oriented toward the center of the toroid such that light is emitted in the direction of the central axis. For example, the housing 305 may be overmolded or positioned over the SMI sensor 310 or the SMI sensor 310 may be otherwise sealed within the housing 305. In some cases, the housing may include multiple components that are bonded together, or otherwise mechanically coupled, to seal the SMI sensor 310 within an internal cavity defined by the housing 305. In some embodiments, the housing 305 may include a transparent material positioned over an emitter portion of the SMI sensor 310 thereby insulating and/or retaining the SMI sensor within the housing while allowing light to pass into and out of the SMI sensor 310. The transparent material may include materials that are selectively transparent to wavelengths of light emitted and/or detected by the SMI sensor 310. For example, the transparent material may include a bandpass filter that selectively allows specific wavelengths of light to pass while blocking other wavelengths of light. Additional examples of such embodiments are described further in relation to FIGS. 4-8.

Figure 4:
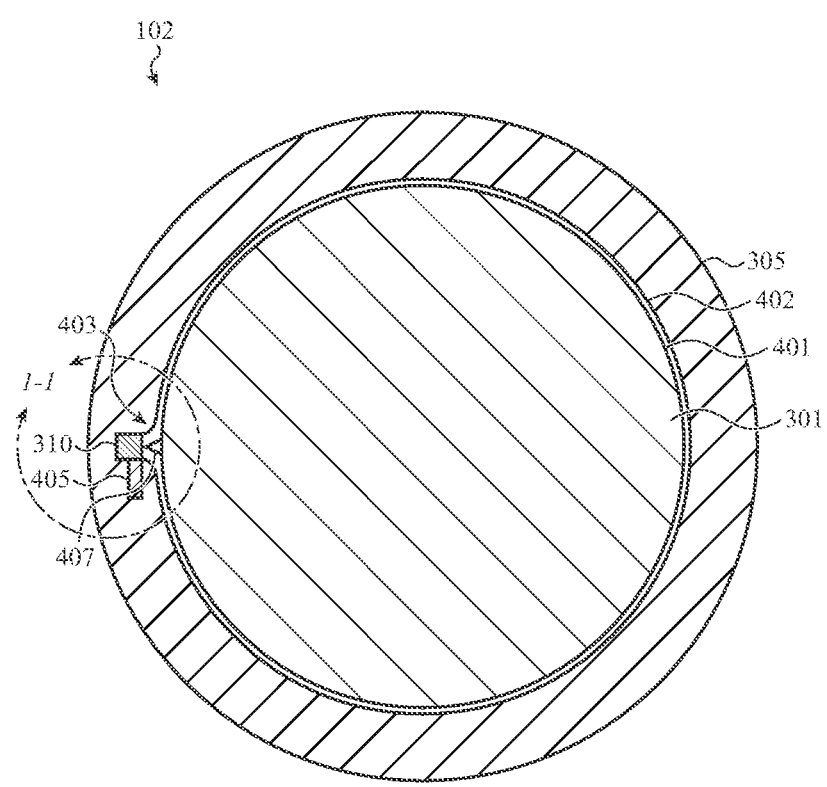
FIG. 4 illustrates a cross-section view taken along line A-A of FIG. 3, showing the wearable device positioned on a finger of a user.

FIG. 4 illustrates a cross-section view of the ring 102, taken along line A-A of FIG. 3. As shown in FIG. 4, the housing 305 defines an interior surface 402 of the ring 102 and a recessed portion 403 containing the SMI sensor 310. The housing 305 fixes the SMI sensor 310 relative to the finger 301 and the recessed portion 403 creates a gap between the SMI sensor 310 and the skin 401 when the ring 102 is worn by the user. The skin 401 may expand into and out of the gap and the SMI sensor 310 may detect this displacement of the skin 401 relative to the SMI sensor 310. The detected displacement may be used to derive one or more physiological conditions about a wearer of the ring 102.

The SMI sensor 310 may detect displacements of the skin surface 401 by emitting coherent light 407 toward the skin 401 and detecting a portion of the coherent light reflected from the skin 401 and back toward the SMI sensor 310. The reflected portion of coherent light may cause interference in the VCSEL and the SMI sensor 310 may output electrical signals based on interference created by the detected portion of the coherent light. The electrical signals may indicate a displacement and/or velocity of the skin 401 of a user.

In some cases, the processing unit 405 receives the SMI sensor 310 signals and tracks expansion and contraction of the skin over time. The processing unit 405 may derive a heartrate for the user based on these displacements. For example, the processing unit 405 may identify a series of peak displacements (e.g., maximum expansion of the skin 401) and/or minimum displacements (e.g., maximum contraction of the skin 401) over a time period. Each peak and/or minimum displacement may be associated with a heartbeat. Then, based on the number of peak displacements and/or minimum displacements detected over the time period, the processing unit 405 may determine a heart rate for the user.

In some cases, the housing 305 may define a cavity within the recessed portion 403 that contains the SMI sensor 310. The SMI devices may be oriented within the cavity such that it is facing inward toward the finger 301. Other support components such as a battery, processing unit, transceiver, and so on may also be positioned within the cavity. In some examples, the recessed portion 403 may include positioning the SMI sensor 310 within the cavity such that an emitting surface of the SMI sensor 310 is offset from the interior surface 402 of the housing 305. That is, the recessed portion 403 may be defined by portions of the housing 305 forming the walls of the cavity and an emitting surface of the SMI sensor 310 positioned within the cavity. In some cases, a cover, encapsulant, sealant or other structure may be positioned over the SMI sensor 310 to protect the emitting surface from dust, debris, oil, moisture, and so on. The housing 305 may define the cavity such that this cover or encapsulant may also be recessed relative to the interior surface 402 of the housing 305. Accordingly, a gap may be maintained between the cover or encapsulant and the SMI sensor 310 to allow for the skin 401 to expand and contract relative to an emitter of the SMI sensor 310. The cover, encapsulant, sealant, or other protective structure may be transmit coherent light emitted by the SMI device 310.

Figure 5A:
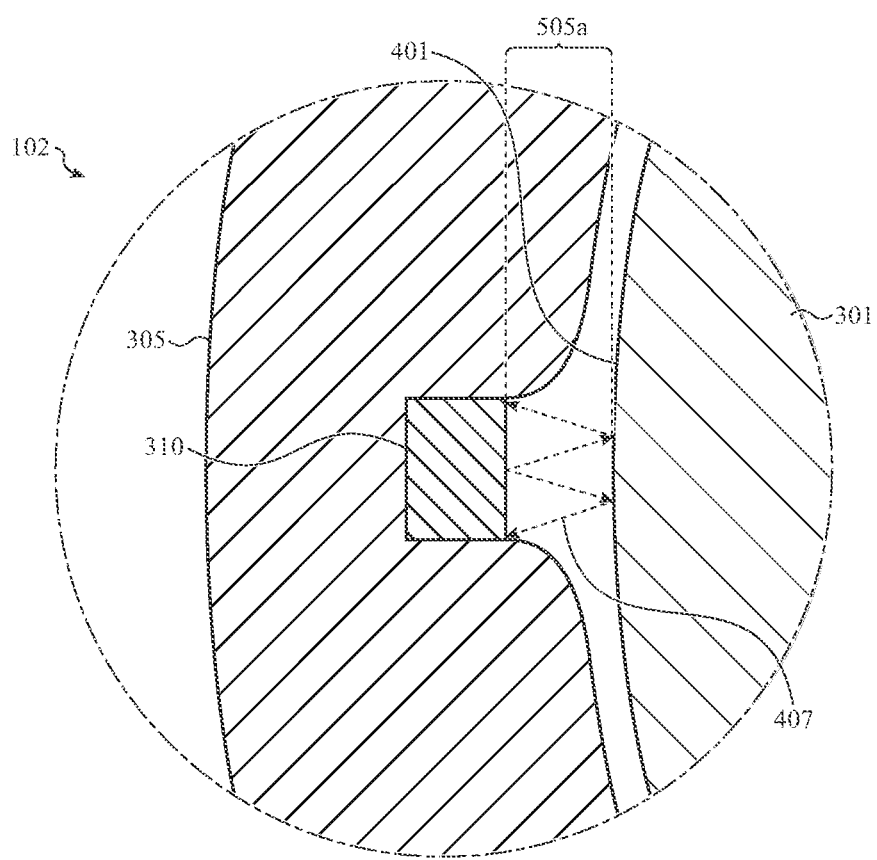
FIGS. 5A and 5B is a illustrate detailed views of section B of FIG. 3, illustrating the positioning and interaction of the SMI sensor relative to a finger of a user.
Figure 5B:
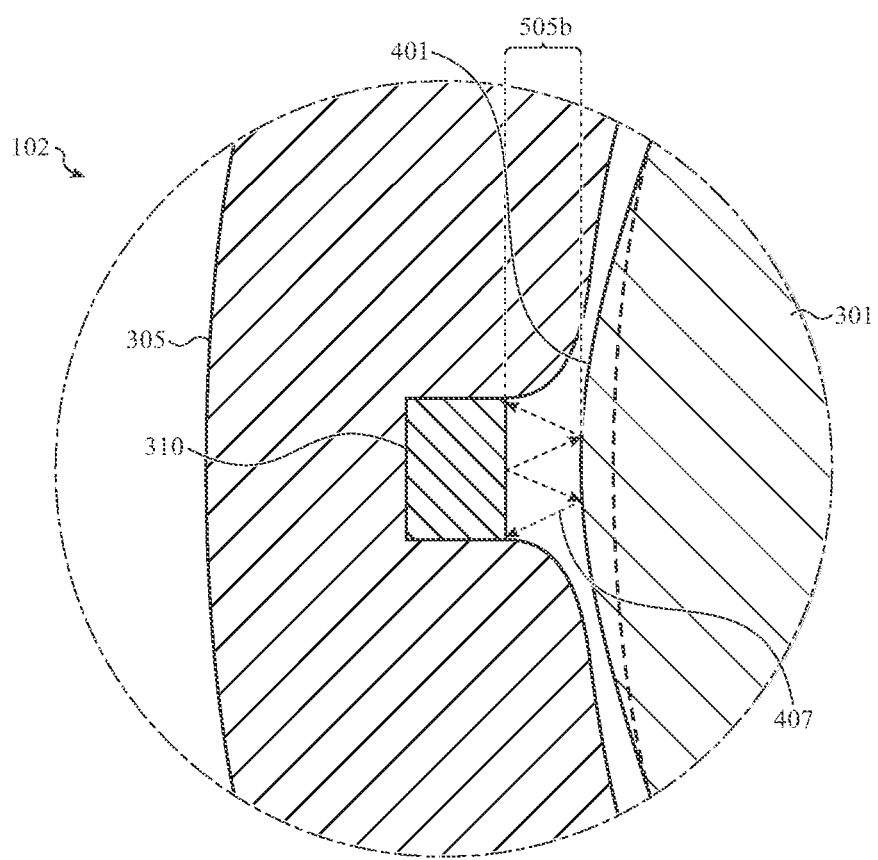

FIGS. 5A and 5B are sections views of the ring 102, showing close-up views of section B of FIG. 4. FIGS. 5A and 5B illustrate measurements of the skin 401 in contracted and expanded states, respectively. As shown in FIG. 5A, the housing 305 may define a recessed portion containing the SMI sensor 310 such that there is a gap between the skin 401 and the SMI sensor 310. That is, there may be a first distance 505a between the SMI sensor 310 and the skin 401. The coherent light 407 from the SMI sensor 310 may travel the first distance 505a to the skin 401, and a portion of the coherent light may reflect from the skin 401 and travel the first distance 505a back to the SMI sensor 310. The SMI sensor 310 may output a first electrical signal correlating to the first distance 505a. This electrical signal may correlate to a first pressure state of blood vessels in the finger 301. As illustrated in FIG. 5A this first distance 505-a may correlate to a low pressure state of the blood vessels (e.g., diastole), and thus, the skin may be in a contracted state.

At a second time, the heart contracts ejecting blood into the vessels of the finger and increasing the blood pressure in the finger 301. As shown in FIG. 5B, the increased pressure in the finger 301 expands the skin 401, and the distance 505 between the skin and the SMI sensor 310 decreases to a second distance 505b. The SMI sensor 310 may output coherent light to detect this second distance 505b of the skin 401, and output an electrical signal that is indicative of this second distance 505b. That is, the change in distance 505 that the coherent light traveled to and from the skin changes the interference in the VCSEL of the SMI sensor 310; this change in the self-mixing interference may be used to determine the distance, a velocity with which the skin 401 moves, and even a change in distance of the skin 401 from the first measurement (e.g., first distance 505a) to the second measurement (e.g., second distance 505b). By taking a series of measurements, repeating patterns can be determined; the number of times the skin expands and contracts (as measured by changes in distance 505 between the skin and the sensor) provides a measure of heart rate. Likewise, blood pressure may be estimated by a change in the distance 505; smaller changes in the distance 505 may correspond to lower blood pressure while larger changes in the distance 505 may correspond to higher blood pressure. In some cases, a blood pressure measurement may be taken by another device during the SMI sensor's 310 operation to provide a resting or initial blood pressure associated with a particular change in the distance 505 of the skin 401 as the heart beats. This may provide for a baseline for estimating changes in blood pressure from future measurements.

Figure 6A:
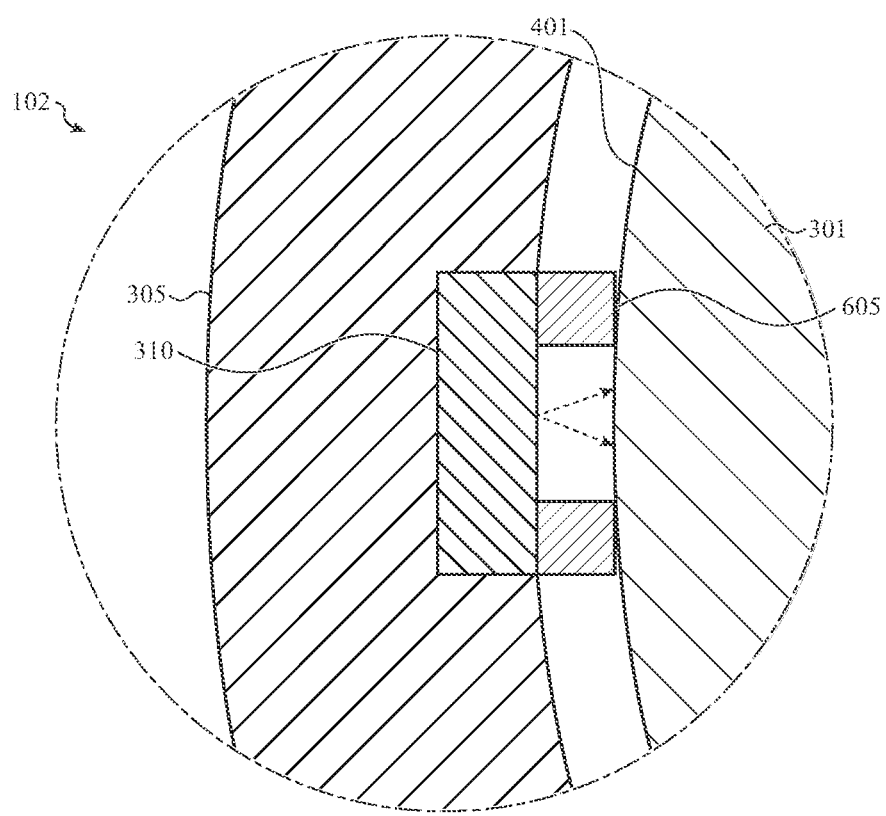
FIGS. 6A and 6B show examples of a wearable device housing that includes an SMI sensor.
Figure 6B:
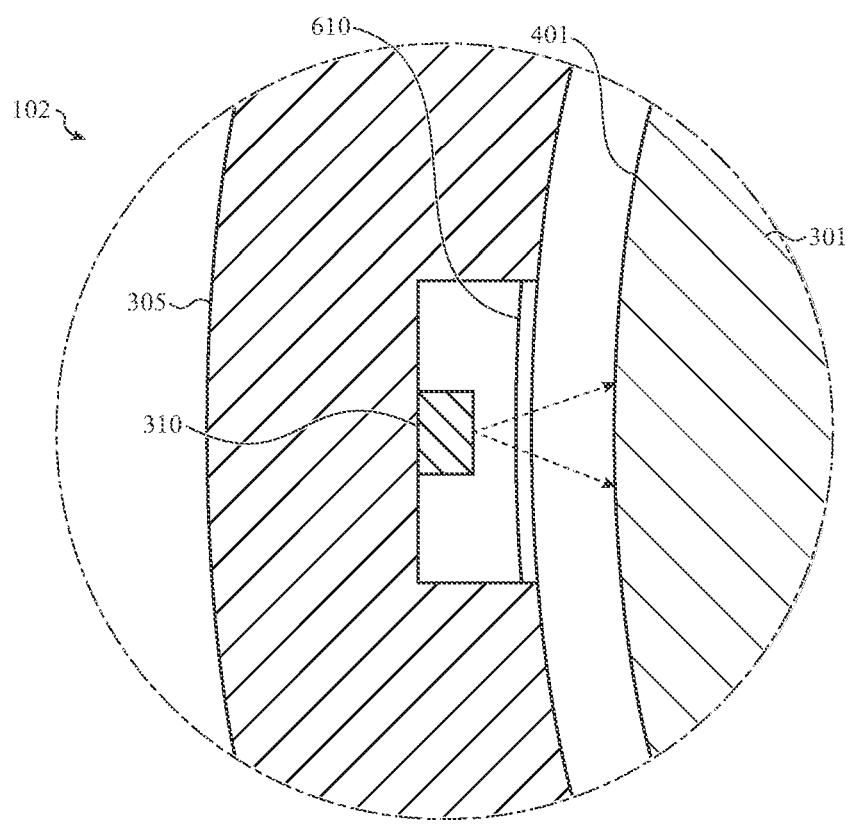

FIGS. 6A and 6B illustrate examples of different embodiments for maintaining a gap between the SMI sensor 310 and the skin 401 of a user's finger 301. As described herein, the skin 401 may expand and contract into and out of the gap in response to a user's heartbeat and the SMI sensor 310 may detect these changes in distance. Accordingly, the housing 305 may include one or more structures or features that maintain an offset between the SMI sensor and skin 401 of a user's finger.

As shown in FIG. 6A, embodiments may include one or more support(s) 605 that contacts the skin 401 to maintain a gap between the SMI sensor 310 and the skin 401. The support(s) may be defined by the housing 305 such as a lip, or other structure that extends past an emitting surface of the SMI sensor 310. Accordingly, the SMI sensor 310 is offset and/or recessed from the support 605. Embodiments also include the support 605 being formed as part of the SMI sensor 310. In these examples, an emitting surface of the SMI sensor 310 may include the support 605 features that maintain a gap between the skin 401 and emitting/detecting portion of the SMI sensor 310.

As shown in FIG. 6B, embodiments may include a flexible cover 610 that contacts the skin 401 to maintain a gap between the SMI sensor 310 and the skin 401. The flexible cover 610 may form a portion of the housing 305 that contains the sensor and may include materials that are transparent to or transmit coherent light to and from the SMI sensor 310. The flexible cover 610 may contact the skin 401 and move (e.g., bend) in response to the skin 401 expanding. Accordingly, the flexible cover 610 may maintain a gap between the SMI sensor 310 and the skin 401 as it expands and or contacts. Some embodiments may include both a support 605 and flexible cover 610 that may be integrated into one component. For example, the housing 305 may define a support structure 605 that surrounds the SMI sensor 310 and projects from an inside surface of the ring 102. The ring 102 may also include a cover 610 positioned within the support structure 605 and covers or seals the cavity containing the SMI sensor 310.

Figure 7:
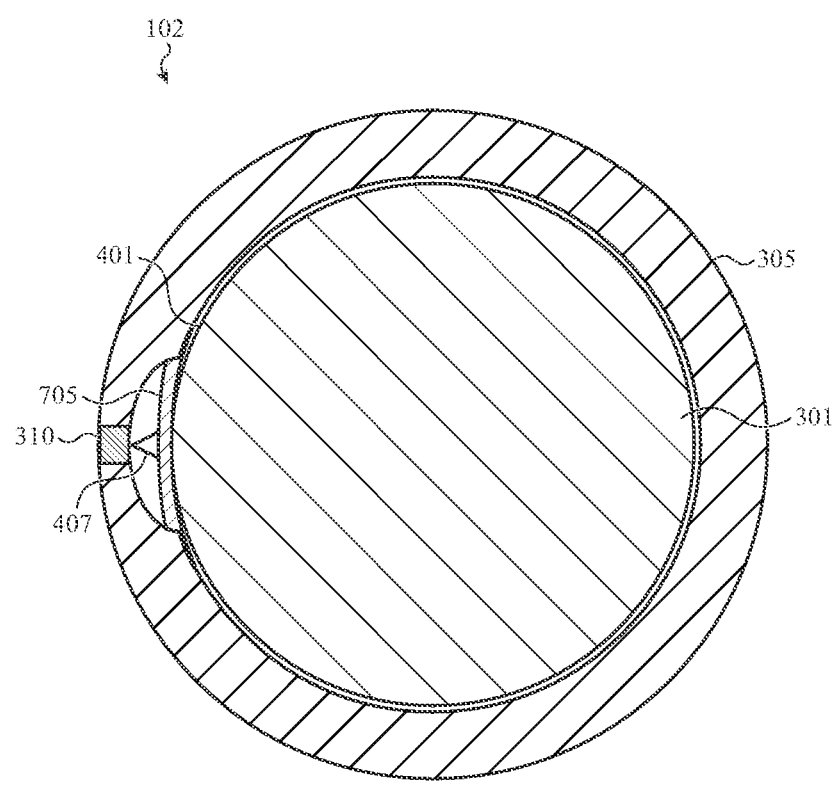
FIG. 7 illustrates an example of a wearable device that includes an SMI sensor and a reflective membrane for directing light emitted from the SMI sensor back to the SMI sensor.

FIG. 7 illustrates an embodiment of the wearable device 102 including a membrane 705 positioned between the SMI sensor 310 and the finger 301. Differences in the skin 401 of users (e.g., reflectivity, tone, texture, age, and so on) may cause variability in the portion of light reflected back to the SMI sensor 310. Thus, some embodiments may include a membrane 705 that contacts the skin 401 and reflects emitted light back to the SMI sensor 310. In some embodiments, the membrane 705 may form a portion of the housing 305. For example, the membrane 705 may include a reflective, retro-reflective or diffusive surface positioned over the portion of the housing 305 (e.g., cavity) containing the SMI senor 310. The membrane 705 may be flexible or otherwise configured to move in response to expansion and contraction of the skin 401. In some cases, the membrane 705 may seal the cavity containing the SMI sensor 310, thereby protecting the SMI sensor 310 from dust, debris, or other contamination.

In operation the SMI sensor 310 may emit coherent light 407 towards the finger 301. A portion of the coherent light 407 may reflect from the membrane 705 and be directed back toward the SMI sensor 310. In this regard, the membrane 705 may reduce variability in the reflected light and/or increase a portion of the light that is reflected to the SMI sensor 310, which may improve displacement measurements of the skin 401. The membrane 705 may be formed from any suitable material including polymers, metals, rubbers or other suitable materials. In some embodiments the membrane includes a coating such as a retro-reflective coating to direct the coherent light back to the SMI sensor 310.

Figure 8:
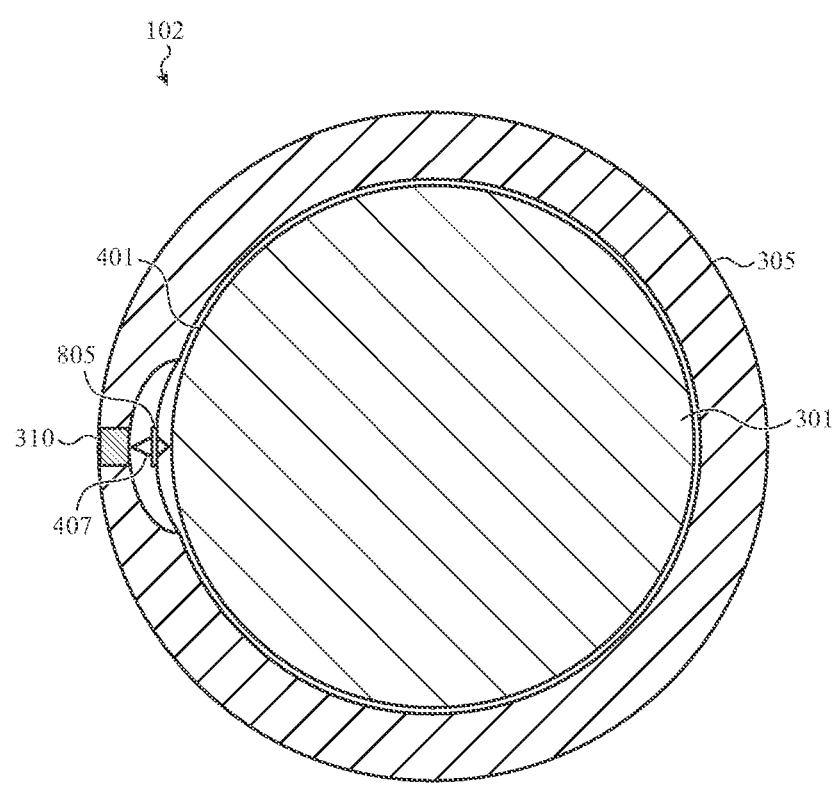
FIG. 8 illustrates an example of a wearable device that includes an SMI sensor and lens for focusing light emitted from the SMI sensor toward a skin surface of a user.

FIG. 8 illustrates an embodiment of the wearable device 102 including a lens 805 positioned between the SMI sensor 310 and the skin 401 of a user. The lens 805 may focus the coherent light 407 emitted from the SMI sensor 310 on the skin 401 of a user to improve optical feedback to the SMI sensor 310. In some cases, the lens 805 may form a portion of the housing 305 and/or be coupled with the housing 305. In other embodiments, the lens 805 may form a portion of the SMI sensor device 310. For example, the lens 805 may be integrated into or coupled with an emitting surface of the SMI sensor 310. The lens 805 may be formed from any suitable material such as glass, plastics, ceramics, crystalline materials, and so on. The lens 805 may have convex, concave, cylindrical, variable curvatures, compound structures, and so on.

Figure 9:
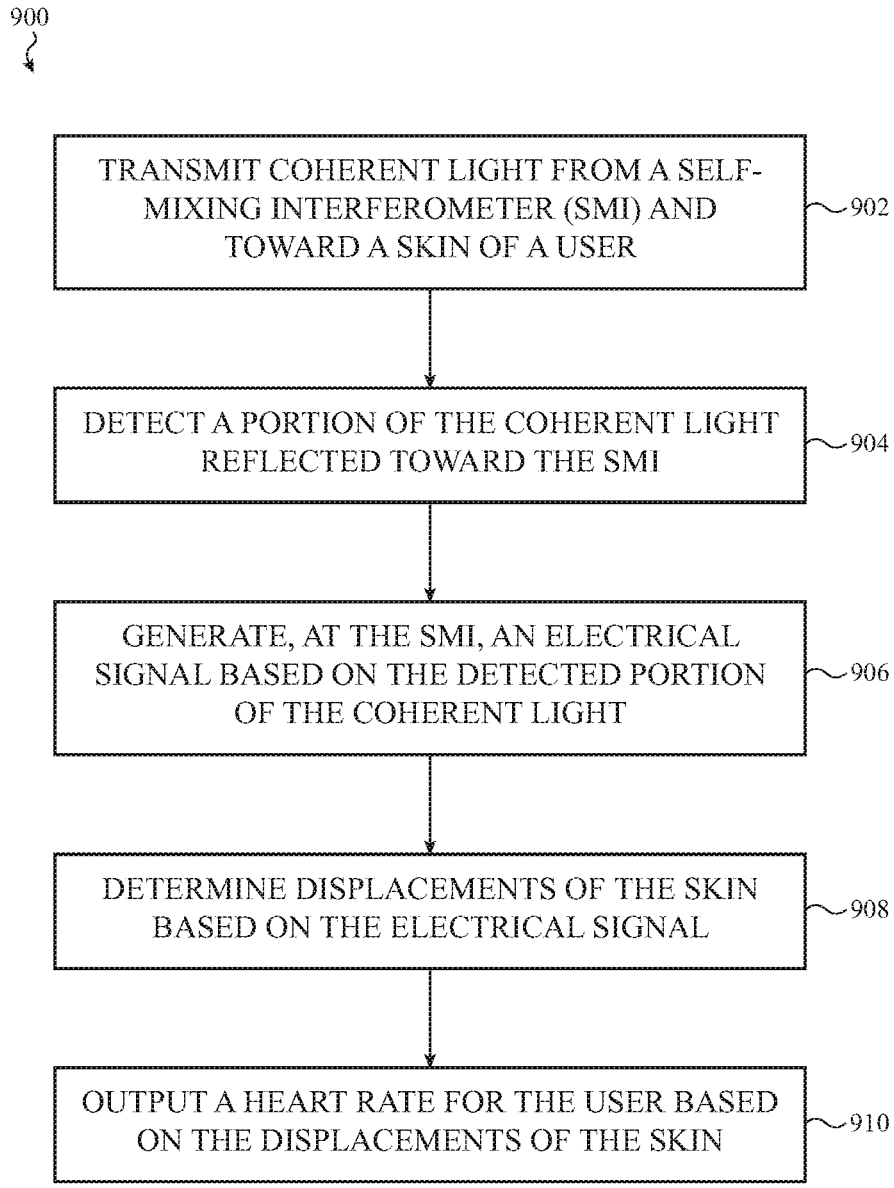
FIG. 9 illustrates an example processes flow for using an SMI sensor to detect one or more physiological parameters of a user.

FIG. 9 illustrates a process flow 900 for operating an SMI sensor to detect one or more physiological conditions of a user such as tracking the movement of the skin of a user. The process flow may be performed by a wearable electronic device such as electronic devices 102 as described herein.

At 902, the process flow 900 may include transmitting coherent light from a self-mixing interferometer (SMI) and towards a skin surface of the user. In some cases, transmitting coherent light toward the skin of a user may include transmitting the coherent light toward a membrane or other structure that is positioned between the skin of the user and the SMI. In some cases, the SMI may include a VCSEL that may be driven by sinusoidal current for wavelength modulation. In other cases, the VCSEL may be direct current (DC) driven.

At 904, the process flow 900 may include detecting a portion of the coherent light reflected from the skin and toward the SMI. In some cases the coherent light may be detected by photo detector of the SMI. The photo detector may be integrated into the SMI or be a separate component positioned at a different location from the SMI.

At 906, the process flow 900 may include generating an electrical signal at the SMI device based on the detected portion of the coherent light. At 908, the process flow 900 may include determining displacements of the skin based on the electrical signal. In cases where sinusoidal driving is employed time domain signal processing may be used to generate electrical signals that indicate displacements of the skin. In cases where DC driving is employed with frequency domain signal processing may be used to generate electrical signals that indicate the unsigned velocity of the skin.

At 910, the process flow 900 may include outputting a heart rate for the user based on the displacements of the skin. That is, the SMI can detect expansion and contraction of the skin. This expansion and contraction can be tracked over time to identify one or more repeating patterns such as a heart rate of a user. In some cases, the amount of expansion and contraction may be used to determine other physiological condition such as a blood pressure of a user as described herein. In further examples, multiple wearable devices each having at least one SMI sensor may be placed at different locations on a user's body. For example, a first wearable device may be positioned around an arm of the user and a second wearable device may be a ring worn on the user's finger. Physiological measurements from a first SMI located at the arm may be correlated to physiological measurements from a second SMI located at the finger. Parameters such as a time difference between the peak pressures at each of the devices may be used to derive additional physiological conditions of a user.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings. Also, when used herein to refer to positions of components, the terms above and below, or their synonyms, do not necessarily refer to an absolute position relative to an external reference, but instead refer to the relative position of components with reference to the figures.

What is claimed is:

1. An electronic device, comprising:
a housing configured to be worn by a user;
a sensor contained within the housing and comprising:
a vertical cavity surface emitting laser (VCSEL) positioned in the housing and configured to output coherent light toward a skin of the user when the housing is worn by the user;
a detector configured to detect a portion of the coherent light that is reflected towards the sensor, and further configured to generate electrical signals corresponding to displacements of the skin, the electrical signals at least partly based on the portion of the coherent light; and
a transmitter operatively coupled with the sensor and configured to transmit data from the electrical signals.

2. The electronic device of claim 1, wherein:
the housing comprises a band configured to wrap around a body part of the user and maintain a gap between the VCSEL and a skin surface of the user when the housing is worn by the user;
the transmitter is further configured to wirelessly transmit the data from the electronic device; and
the data comprises a time indicator that associates a displacement of the skin with a relative time of an electrical signal of the electrical signals generated by the detector.

3. The electronic device of claim 1, further comprising a processing unit configured to determine a heart rate of the user from the electrical signals.

4. The electronic device of claim 3, further comprising a display configured to output a visual representation of the heart rate.

5. The electronic device of claim 1, wherein the detector is configured to detect the portion of coherent light that is reflected from the skin of the user.

6. The electronic device of claim 1, further comprising a membrane positioned between the emitter and the skin of the user; wherein:
the detector is configured to detect the portion of coherent light that is reflected from the membrane.

7. The electronic device of claim 6, wherein:
the membrane contacts the skin of the user when the housing is worn by the user; and
the membrane is configured to move in response to movement of the skin.

8. The electronic device of claim 6, wherein the membrane comprises a reflective surface configured to direct the coherent light towards the detector.

9. The electronic device of claim 1, further comprising a lens coupled with the housing and configured to focus the coherent light on the skin when the housing contacts the skin of the user.

10. The electronic device of claim 1, wherein:
the housing comprises a skin support configured to contact the skin of the user; and
the emitter is offset from the skin support.

11. The electronic device of claim 1, wherein the emitter and the detector comprise a same structure.

12. An electronic device, comprising:
a sensor comprising:
an emitter configured to output coherent light toward a skin of a user when the electronic device is worn by the user; and
a detector configured to detect a portion of the coherent light reflected from the user and generate electrical signals based on the portion of the coherent light;
a housing containing the sensor and configured to position the emitter at a first distance from the skin of the user, the housing comprising:
a user interface configured to contact the skin of the user; and
a membrane or a lens positioned between the emitter and the skin when the housing contacts the user; and
a transmitter positioned within the housing and operatively coupled with the sensor, the transmitter configured to transmit physiological data based on the electrical signals.

13. The electronic device of claim 12, wherein the user interface is positioned adjacent to the sensor and is configured to contact the skin of the user, thereby maintaining a gap between the skin and the emitter.

14. The electronic device of claim 12, wherein the membrane is configured to reflect the coherent light outputted by the emitter back to the detector.

15. The electronic device of claim 12, wherein:
the emitter is a vertical cavity surface emitting laser (VCSEL);
the detector is the VCSEL; and
the VCSEL is configured to output the electrical signals based on a difference between the outputted coherent light and the portion of coherent light reflected from the user.

16. The electronic device of claim 12, wherein:
the detector comprises a resonant cavity photodetector; and
the resonant cavity photodetector comprises a circular structure positioned around the emitter.

17. A method for tracking movement of a skin of a user, the method comprising:
generating coherent light within a vertical cavity surface emitting laser (VCSEL) of a self-mixing interferometer (SMI) and emitting the coherent light towards a skin surface of the user;
detecting, using the SMI, a self-mixing interference between the generated coherent light and a portion of the coherent light reflected toward the SMI;

generating, at the SMI, an electrical signal based on the self-mixing interference;

determining displacements of the skin based on the electrical signal; and outputting a heart rate for the user based on the displacements of the skin.

18. The method of claim 17, wherein:

the displacements of the skin are tracked for a first duration; and outputting the heart rate comprises identifying heartbeats of the user for the first duration.

19. The method of claim 17, further comprising displaying a visual output of the heart rate to the user based on the outputting.

\* \* \* \* \*